United States Patent [19]

Roup

[11] Patent Number: 4,466,794
[45] Date of Patent: * Aug. 21, 1984

[54] DENTAL SIMULATOR

[76] Inventor: Walter G. Roup, 2425 Underwood, #360, Houston, Tex. 77030

[*] Notice: The portion of the term of this patent subsequent to Jan. 11, 2000 has been disclaimed.

[21] Appl. No.: 420,645

[22] Filed: Sep. 21, 1982

Related U.S. Application Data

[63] Continuation of Ser. No. 176,198, Aug. 7, 1980, Pat. No. 4,368,041.

[51] Int. Cl.³ .............................................. A61C 19/04
[52] U.S. Cl. ........................................ 433/69; 433/73
[58] Field of Search ...................... 433/69, 68, 73, 71, 433/55, 57, 58

[56] References Cited

U.S. PATENT DOCUMENTS

| | | | |
|---|---|---|---|
| 1,338,918 | 5/1920 | Hall | 433/58 |
| 1,464,474 | 8/1923 | Homer | 433/55 |
| 2,418,648 | 4/1947 | Kile | 433/69 |
| 2,814,876 | 12/1957 | Stuart | 433/73 |
| 3,074,166 | 1/1963 | Skallerup | 433/69 |
| 3,078,584 | 2/1963 | Cohn | 433/73 |
| 3,131,475 | 5/1964 | Craigo et al. | 433/71 |
| 3,423,834 | 1/1969 | Irish | 433/73 |
| 3,452,439 | 7/1969 | Lee | 433/55 |
| 4,126,938 | 11/1978 | Lee | 433/69 |

Primary Examiner—John J. Wilson
Attorney, Agent, or Firm—David Alan Rose; David S. Wise

[57] ABSTRACT

The simulator includes an upper and lower facebow for mounting on a patient to record and later reproduce the three dimensional movements of the patient's mandible. The upper frame has two receptacles mounted thereon having a bore opening toward the anterior portion of the facebow. A molding material is disposed within the receptacles and the lower frame has two styli projecting into the receptacles for indenting the molding material to make an innerocclusal record during the movement of the patient's mandible. The frames are then removed and dental casts are affixed to the frames. The innerocclusal record formed in the molding material is used to reproduce all of the patient's mandibular movements.

5 Claims, 16 Drawing Figures

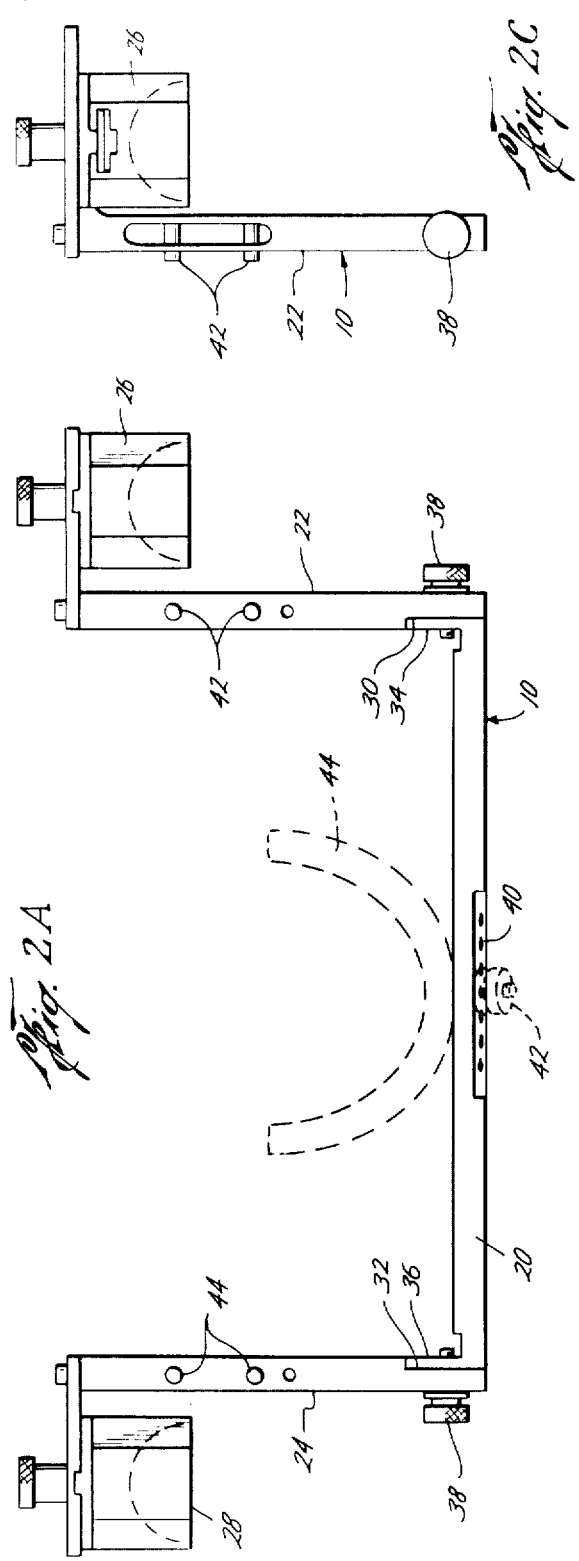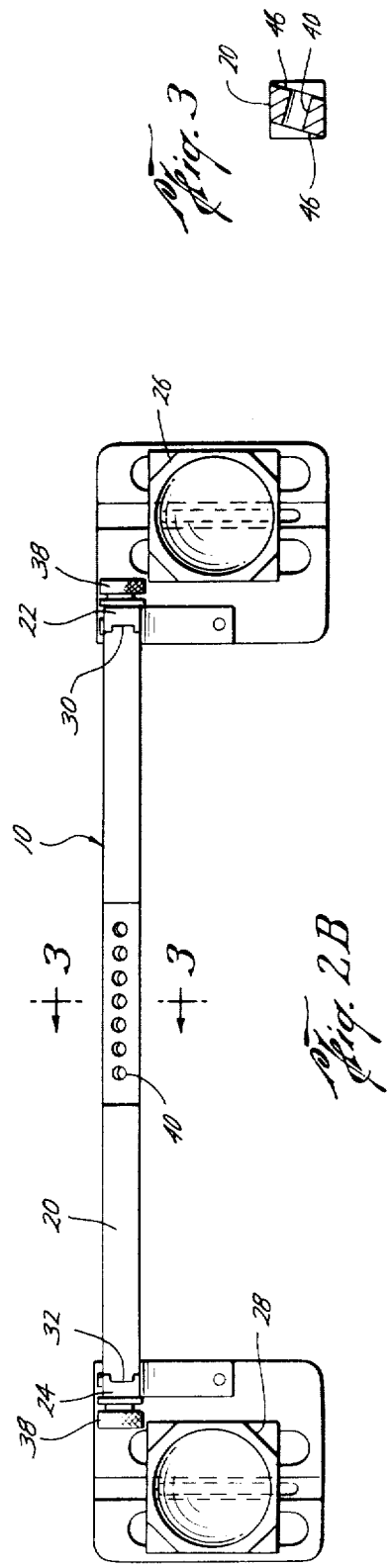

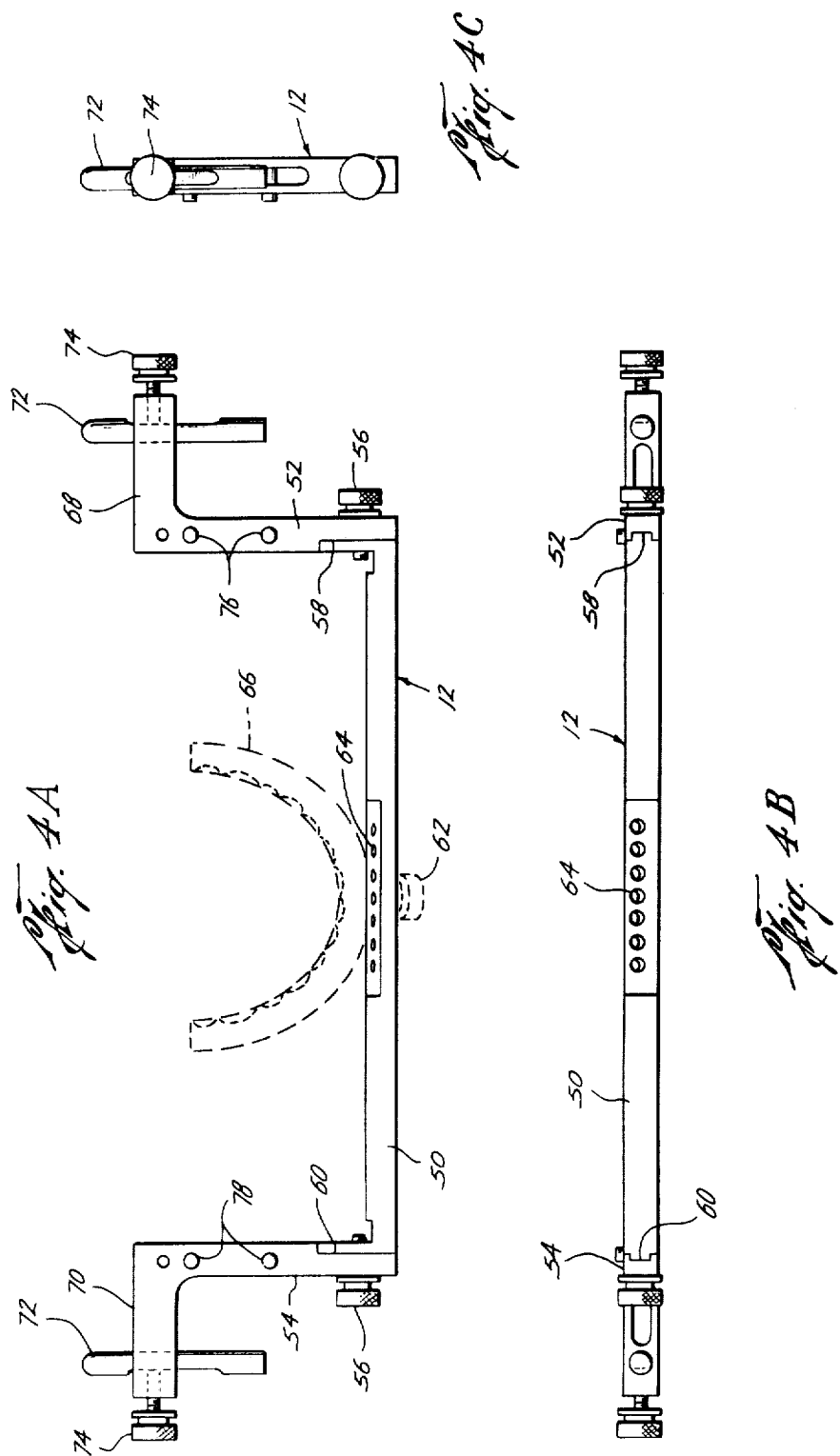

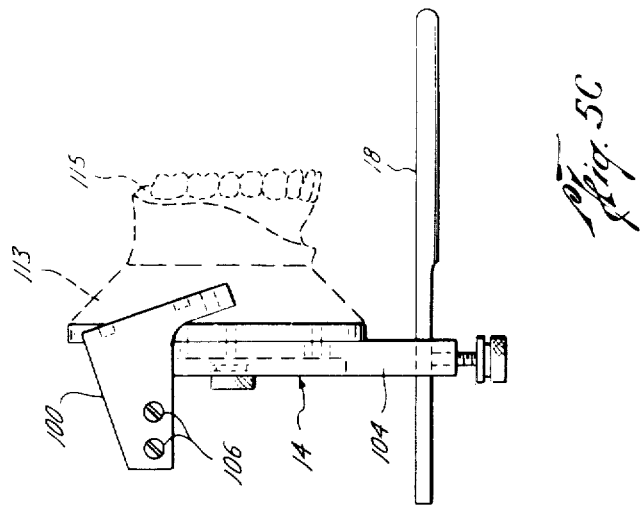
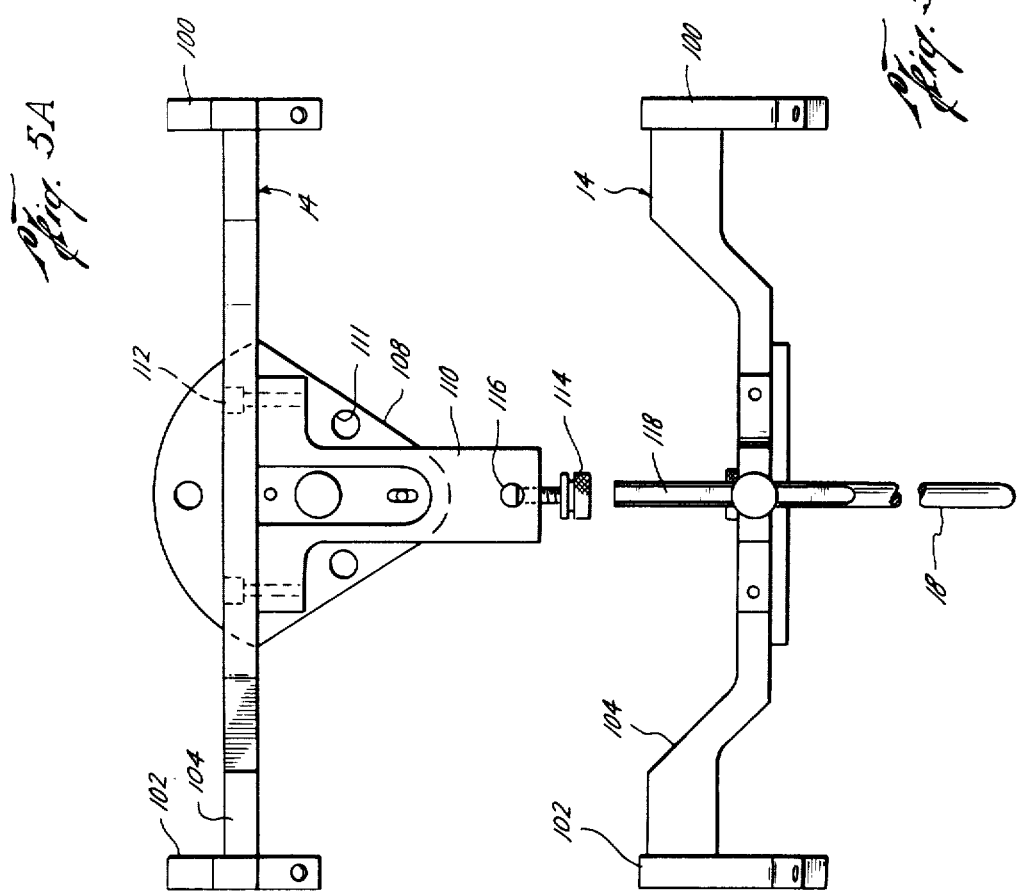

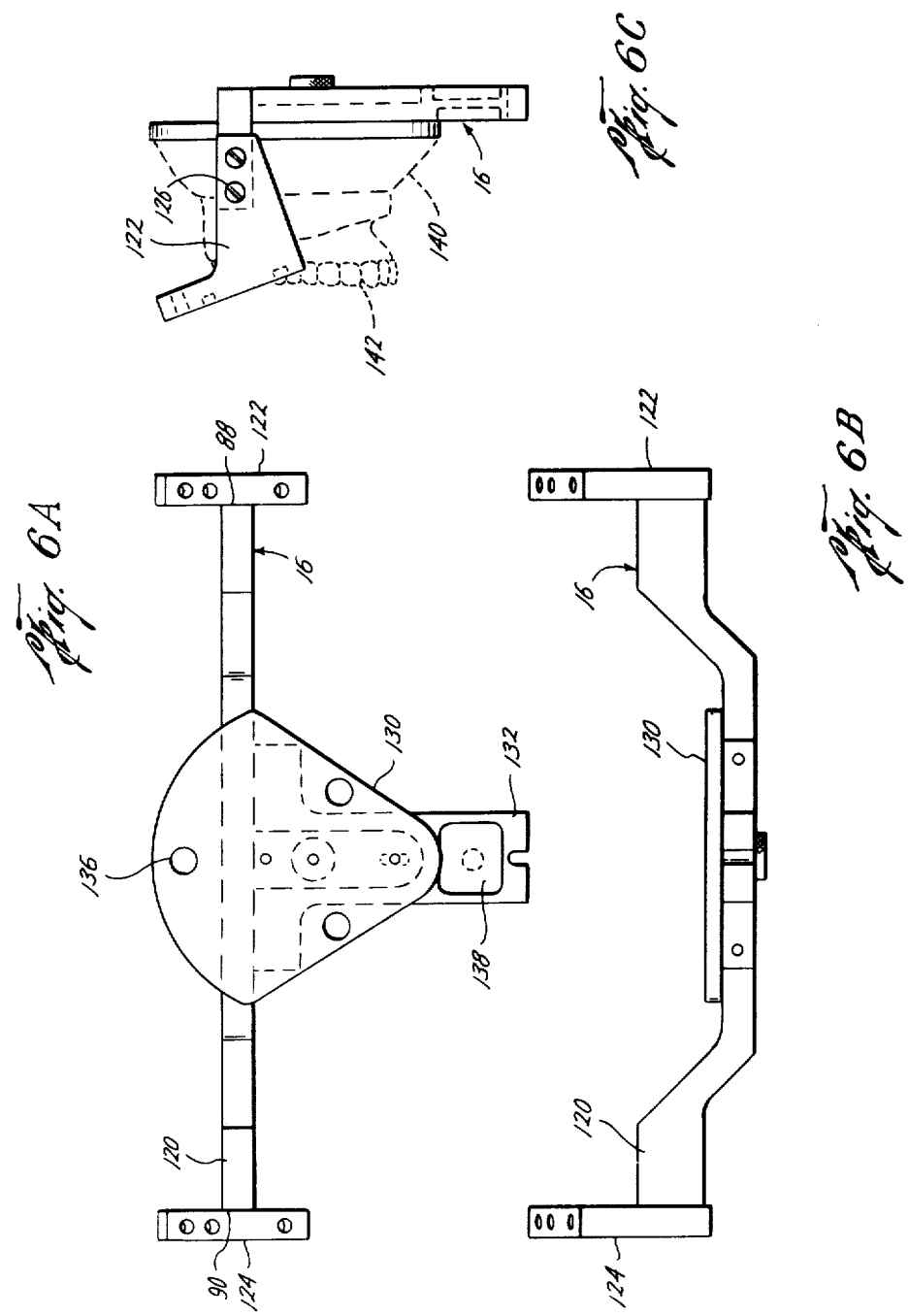

DENTAL SIMULATOR

This is a continuation of Ser. No. 176,198, filed Aug. 7, 1980, U.S. Pat. No. 4,368,041, Jan. 11, 1983.

TECHNICAL FIELD

This invention relates to dental articulators or relators, and more particularly to apparatus for recording and simulating the movement of the jaws of a dental patient for evaluation, diagnosis, and treatment of occlusal problems and for dental rehabilitation.

BACKGROUND OF THE ART

Function, aesthetics, and comfort are prime objects of restorative dentistry, and the ability to treat occlusal problems is directly related to the ability to capture and transfer jaw motion to the restoration. Existing conditions of the patient must be analyzed by means of a functional method and the mere relation of the teeth to each other is not enough. Unless the relationship satisfies the functional requirements of the whole mouth, it may become a destructive function, creating a metabolic demand in excess of the normal requirements of the mouth.

To achieve these objectives, and to prevent trauma, wear and loss of centric relation contacts, the cuspal elements must be free to travel in and out of centric relation closure and free to perform their functions without interference or lateral stresses. The height, position, and relation of the cuspal elements are determined by studying the determinants of occlusion, namely, ridge and groove direction determinants (axis-orbital horizontal plane), cusp height and fossae depth determinants (sagittal plane), and determinants of the lingual concavity of upper anterior teeth. Since the length or height of the cusps is influenced by the condyle path, and the position and form of the cusps are determined by the Bennett movement which must harmonize with the lateral shift, it is necessary to observe the interferences between centric relation and centric occlusion position and the cusp pathways during eccentric mandibular movements to determine the formation of corrective measures. See *Evaluation, Diagnosis, and Treatment of Occulusal Problems* by Peter E. Dawson (1974) and *Volume One: Mouth Rehabilitation Clinical and Laboratory Procedures* by Max Kornfeld (2d Ed. 1974).

Because the musculature motivates the movement of the mandible and the temporomandibular joint determines the movements, the determinants of the mandibular movements that dictate the occlusal morphology must be obtained and reproduced correctly to properly treat abnormal occlusion. Unless these varieties of motions can be accurately recorded and reproduced through laboratory registrations of the study casts of the teeth, occlusal corrections may become necessary.

Laboratory duplication includes making study casts of the maxillary and manibular teeth. Registrations are taken of the jaw movements of the patient by one instrument and are later transferred to a second instrument. The casts are them mounted to the second instrument to the correct axis and the second instrument is used to simulate the movements of the patient's jaws in the laboratory to permit the review of the occlusal relationships of the patient's teeth. Various prior art instruments have been used to record and attempt to duplicate jaw movement including the pantograph, stereographic instruments, articulators, and relators.

The pantograph graphically records the various positions and movements of the mandible and then the resulting graphs are utilized to adjust an articulator which attempts to reproduce the paths of the patient's movements. The pantograph relies upon the hinge axis even though the hinge axis has control only along the border paths when we masticate. The pantograph has two facebows with six recording slides and six styli that scribe the paths of the centers of rotation of the mandible. The hinge axis if first located, and then an innerocclusal record is taken at centric relation or centric occlusion. The pantograph then graphically records the movements of the jaw. In making these records, the clutches mounted to the pantograph have to be separated vertically so that there will be no tooth guidance during the registrations, and at the same time separated a minimum distance to reduce the error. After a record of the jaw movements has been registered and the orbital guide set, the arms of the pantograph are locked together and the entire assembly is removed intact from the patient and is transferred to the mounting frame or jig that holds the facebow in proper relation to the adjustable articular while the attaching stone sets.

There are two types of articulators, the semiadjustable articulator and the adjustable articular. The semiadjustable articulator is often referred to as the checkbite articulator which reproduces the horizontal condyle paths from an innerocclusal record made at centric relation and a bite record made in the protrusive position. The resultant path is a straight line between the two points. Lateral pathways are set from the centric bite record (innerocclusal record) and records are made in the left lateral and right lateral jaw positions. The semiadjustable instrument can accurately record the hinge axis but cannot record the full range of lateral and protrusive condylar movements. Further, semiadjustable instruments do not precisely record the Bennett shift. With adjustable articulators, a more complete preoperative occlusal analysis is possible than is possible with semiadjustable articulators. The improvement in accuracy is the difference between straight line vs. curve pathways plus the differences of timing of the Bennett shift.

A stereographic instrument may be used in place of the pantograph for taking registrations which are subsequently transferred to another instrument such as the TMJ Articulator or the Gnathic Relator. The stereographic instrument generally includes upper and lower intraoral clutches having a central bearing point therebetween. An innerocclusal record is made in centric relation or centric occlusion. Recordings are then made by indenting three or four points, mounted on one clutch, into doughy self-curing acrylic on the surface of the opposite clutch and then moving the mandible. When the stereographic record is completed, the acrylic guide paths are allowed to set hard. In using the TMJ Articulator, the stereographic clutches are mounted on the TMJ Articulator using the centric bit record (innerocclusal record). A doughy mixture of TMJ acrylic is placed in plastic receptacles at the condyles and the condyles are guided by moving the points through the paths made by the indentations. After the condyle paths are recorded, the casts are mounted in place of the clutches. The Gnathic Relator is a device that uses the stereographic clutches after anterior guidance has been corrected in the mouth. The clutches are screwed into the study casts thereby permitting the border pathways to be reproduced by hand using the handheld models. Further description of the above is found in *Evaluation, Diagnosis, and Treatment of Occulusal Problems,* by Peter E. Dawson (1974) at pages 124-131 and is incorporated herein by reference.

Many practical problems have been encountered using such prior art techniques and instruments. Pantographic tracings are not more accurate than the paths of movement that the operator records. Many pantographic erroes result from failure to achieve a true terminal hinge condyle position during any part of the tracing. Further, there is the fear of recording a protrusive lateral path instead of the straight lateral border path.

Another disadvantage of pantographic devices is that the tracings must be made at a considerably opened vertical dimension to make room for the clutches. It is essential that the terminal hinge axis be recorded precisely or the incorrect axis of the closure will introduce errors. It is also probable that in some mouths, at least, the border movements are different at the opened position from what they are at the correct vertical position.

Errors in mounting of pantographic devices are common and easy to make. The slightest movement of either clutch produces a magnified error at the tracing plate. Studies have shown that reproducibility of pantographic tracing is seldom achieved.

One of the most important purposes of an articulator is to relate the upper and lower models to the correct horizontal axis. Semiadjustable articulators do not permit a correct relationship to the axis of closure. Sizeable errors are introduced into all aspects of occlusal form when incorrect horizontal and vertical axes are not used. The problem with simple hinged type articulators is that the only movements that they can make are movements the patient cannot make.

Tooth relations on the articulator will not be the same as in the mouth unless the opening-closing hinge in centric relations are the same on the articulator as in the patient's mouth. The articulator must reproduce the same relation of the casts to the axis of the instrument that the teeth have to the axis of the manible. Unless the casts can be occluded by closing them on the same arc of closure as that exhibited by the patient, erroneous conclusions may be drawn concerning existing patterns and the need for restorative procedures for the patient.

The stereographic instrument requires intraoral clutches which must be fitted inside of the patient's mouth. The central bearing point must be properly sized or the vertical dimension may be in error. No recordings are made other than in the closed position since an open position will cause the pointers to lift from the acrylic. Further, if the intraoral clutches are not mounted in the mouth in the same position as on the study casts, error will be introduced.

Both the pantographic devices and stereographic instruments require an innerocclusal record made in centric relation or centric occlusion. Such an innerocclusal record is required to accurately orient and relate the maxillary and mandibular casts on the articulator. Unless the casts are properly oriented, upper to lower, on the articular, the recordings cannot be properly reproduced. It has been found to be difficult to obtain an accurate bite in centric relation or centric occlusion.

Transfer is also required using the stereographic instrument. The TMJ articulator relies upon the accurate transfer of the registrations of the stereographic instrument. Any time such a transfer is made and recordings have to be duplicated, errors arise.

A great amount of time is often wasted on procedures that have little or no value in specific cases. The articulator should be used to achieve precise reproduction of condylar pathways and not become subservient to the particular techniques such as the transfer of the recordings to a duplicator of the jaw movements.

Mandibular movements are three-dimensional in character and have been found to be complex. The envelope of motion has anterior, posterior, and lateral limits, and there is a sequence of motion from one position to the other. Not only do the joints rotate in the vertical, horizontal, and sagittal planes, but they are capable of bodily side shift (the Bennett movement) which adds another motion to the complexity of movement. When rotation and translation are combined, there is no constant axis of control. The axis that changes is called the instantaneous axis of rotation, and it is only in control for an instant and can only be located when motion is stopped. If the instantaneous centers cannot be located, there is no way of plotting the functional envelope of motion and the border paths of the complete envelope must be used. The task of duplicating such mandibular movements has been found to be lacking in prior art devices.

The present invention overcomes the deficiencies of pantographs, stereographic instruments, articulators and relators by eliminating the necessity of an innerocclusal record at centric relation or centric occlusion and by eliminating the transfer of the recordings to a mechanical duplicator of the movements of the jaw. Further, the present invention provides a three-dimensional recording which is more repeatable and readable than those that exist in the prior art. The present invention becomes a substitute for the jaws in which all occlusal determinants and the opening and closing axis relations are precisely incorporated. The present invention does not require the location of the hinge axis or the establishment of the axis-orbital plane or centric relation. No interpolation is required in its recordings and duplication of jaw movement. The present invention permits reproduction of the patient's mandibular movements, accurate record and check of centric relation, alteration of the vertical dimension with certainity, recordation of the limit of the maximal occlusal opening, minimization of the adjustment in the mouth during restoration, and duplication of all arcs of closure. Other objects and advantages of the present invention will become apparent from the following description.

DISCLOSURE OF THE INVENTION

The present invention includes a maxillary and mandibulary facebow, a maxillary and mandibular support and an incisal pin. Receptacles are mounted on the ends of the side arms of the maxillary facebow, and the side arms of the mandibular facebow have styli disposed thereon projecting into the receptacles of the maxillary facebow. Means are located at the mid-point of both the facebows for the attachment of labial cores and/or bite rims.

The labial cores are formed on study models of self-polymerizing acrylic and are lined with a soft rubber base material for comfort is used as facial cores. These are constructed such that there will be no interference with the movement of the mandible. These cores are on the maxillary and mandibular facebows, respectively, and have mounting screws for attachment to their respective facebows placed at slightly converging angles. This separates the facebows to prevent interference posteriorly. At this stage the patient has the cores and facebows positioned such that the mandible stylus is positioned in the center of the maxillary receptacle. This is further centered and adjusted by means of adjustment screws on the upper receptacle. Self-polymerizing plastic is placed in the maxillary receptacles and the patient is instructed to open wide, protrude right and left, lateral excursions and retrude the mandible in repeated movements until the plastic is rigid. At this point an innerocclusal record at any position is taken using wax, acrylic, zinc oxide eugenal plaster or any other suitable material.

The completed apparatus is removed. Master casts, study casts, or working casts can now be positioned in the occlusal records. The maxillary and mandibular supports with mounting rings are attached to the maxillary and mandibular facebows by means of connector screws. These are screwed in position on both sides and the incisal pin is positioned. The casts are mounted by plastering both the upper and lower in place. The anterior sections of the maxillary and mandibular facebows with the facial cores or bite rims are removed by means of disconnect screws. The remaining apparatus becomes the working articulator. No transfer to another instrument is necessary. The movements of which are exact duplications of the patient's mandible. Additional working models can be added to the instrument by removing the prior models are using the innerocclusal record to position the new models.

BRIEF DESCRIPTION OF THE DRAWINGS

For a detailed description of a preferred embodiment of the invention, reference will now be made to the accompanying drawings wherein:

FIGS. 2A, 2B, and 2C are plan, elevation, and side views, respectively, of the maxillary facebow shown in FIG. 1;

FIG. 3 is a section view of the maxillary facebow of FIG. 2B taken at plane 3—3 in FIG. 2B;

FIGS. 4A, 4B, and 4C are plan, elevation, and side views, respectively, of the mandibular facebow shown in FIG. 1;

FIGS. 5A, 5B, and 5C are plan, elevation and side views, respectively, of the maxillary support shown in FIG. 1;

FIGS. 6A, 6B, and 6C are plan, elevation, and side views, respectively, of the mandibular support shown in FIG. 1;

DESCRIPTION OF THE PREFERRED EMBODIMENT

Figure 1:
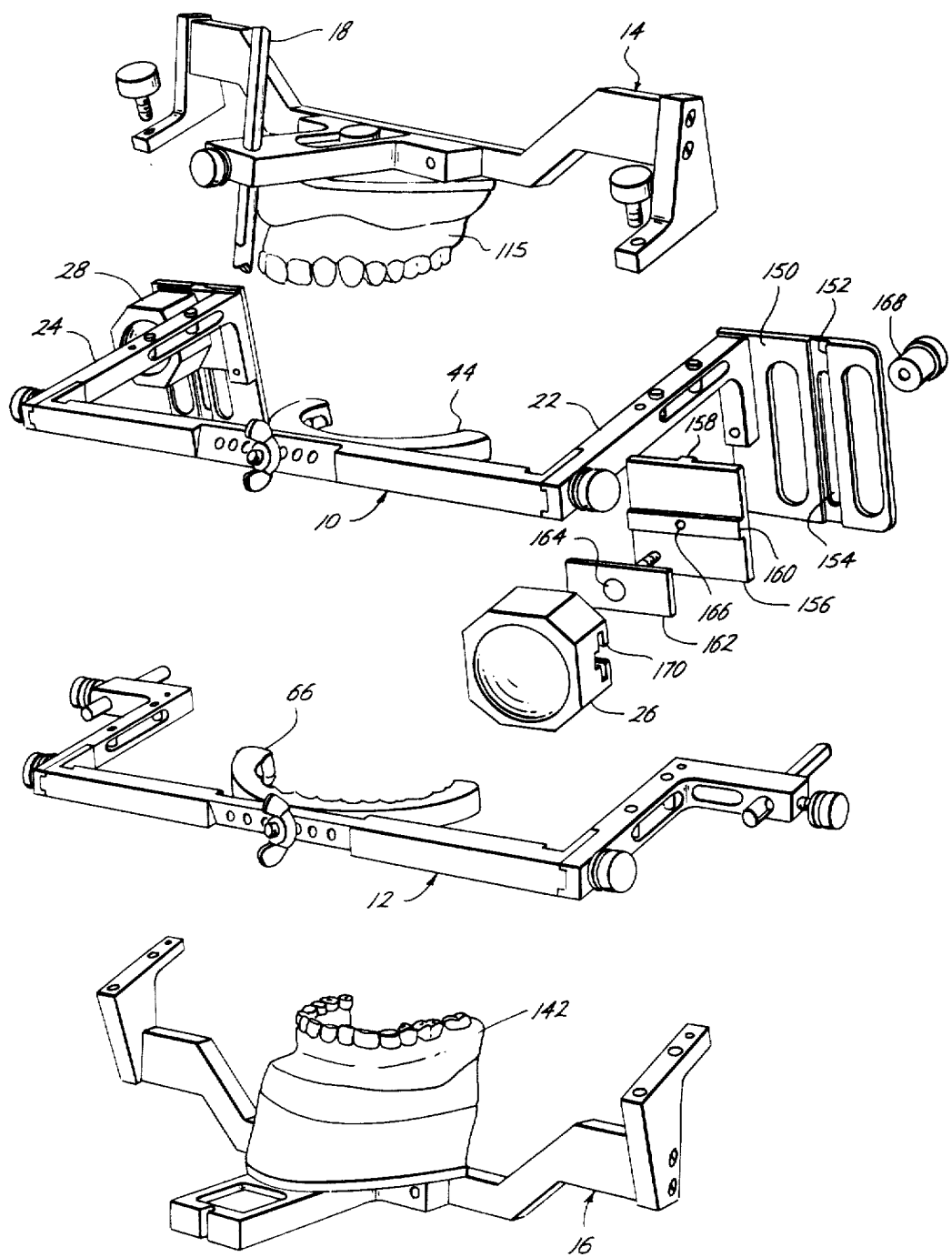
FIG. 1 is an exploded view of the dental simulator of the present invention.

Referring initially to FIG. 1, there is illustrated the simulator of the present invention shown in an exploded view. The simulator includes maxillary and mandibular facebows 10, 12, maxillary and mandibular supports 14, 16, and incisal pin 18.

Referring now to FIGS. 2A, 2B, and 2C, maxillary facebow 10 includes a cross-bar 20 and two side arms 22, 24. Receptacles or mold cups 26, 28 are mounted on one end of each of the side arms 22, 24, respectively. Side arms 22, 24 include vertical guide pins 42, 44, respectively, located by approximately their mid-portion for the alignment of upper support 14 as hereinafter described. Dove-tailed slots 30, 32 with square seats are disposed in the slotted ends of side arms 22, 24 opposite receptacles 26, 28 for matingly engaging opposing dove-tailed protrusions 34, 36 on the ends of cross-bar 20. Lock screws 38 attach side arms 22, 24 to each end of cross-bar 20 at dove-tailed slots 30, 32.

Referring again to FIG. 1, receptacles 26, 28 are mounted on side arms 22, 24 by means of brackets 150 secured to the ends of side arms 22, 24. Means are provided to permit both vertical and horizontal adjustment of receptacles 26, 28 on brackets 150. Brackets 150 include a vertical groove 152 which has a vertical slot 154. An adjustment plate 156 has a vertical projection 158 and a horizontal projection 160. Vertical projection 158 is slidingly received within vertical groove 152. Receptacle 26 has a T-shaped horizontal channel 170 on its back side for receiving bar 162 and horizontal projection 160. A bolt 164 is affixed to bar 162 and passes through an aperture 166 in plate 156 and through slot 154. Nut 168 is threaded onto bolt 164 to mount receptacle 26 to bracket 150. By loosening nut 168, projection 158 is permitted to slide in groove 152 for the vertical adjustment of receptacle 26 and projection 160 is permitted to slide in channel 170 for horizontal adjustment. Receptacle 28 is adjustably mounted on a like bracket disposed on side arm 24.

Referring now to FIGS. 2 and 3, cross-bar 20 includes a series of holes 40 at its mid-point for receiving holder nut and screw 42 for attaching labial core 44. The axes of holes 40 are slanted at a downward angle to the plane of the surface of cross-bar 20. Such downward slant positions the labial core 44 in proper position for engagement with the patient's teeth. Cross-bar 20 is ground down to form a plane 46, at the entrance and exit of holes 40, which are perpendicular to the axis of the holes 40.

Referring now to FIGS. 4A, 4B, and 4C, mandibular facebow 12 is similar in construction to that of maxillary facebow 10. Mandibular facebow 12 includes two side arms 52, 54 attached to cross-bar 50 by lock screws 56 passing through dovetailed slots 58, 60. Side arms 52, 54 also include vertical guide pins 76, 78, respectively, at approximately their midportion for alignment for mandibular support 16 as hereinafter described. Support arms 68, 70 are mounted on the ends of side arms 52, 54, respectively, and include apertures for receiving studs or styli 72. Styli 72 are rounded for making impressions in the acrylic to be placed in mold cups 26, 28 as hereinafter described. Adjustment screws 74 are threadingly mounted in support arms 68, 70 for adjusting the protrusion of styli 72 into mold cups 26, 28.

Cross-bar 50, like cross-bar 20, also includes a series of holes 64 at its mid-point for receiving holder nut and screw 62 for attaching labial core 66. The axes of holes 64 are slanted upward to the plane of the surface of cross-bar 50 in the same manner as holes 40 are slanted downward in cross-bar 20. Thus, the axes of holes 40 and 64 converge towards the patient's mouth.

Referring now to FIGS. 5A, 5B, and 5C, maxillary support 14 for maxillary facebow 10 includes end brackets 100, 102 supporting arch 104. Mounting screws such as at 106 affix the ends of upper support arch 104 to brackets 100, 102. A maxillary plate 108 is mounted on bracket 110 which in turn is disposed at the mid-point of upper support arch 104 by an appropriate fastening means such as by screws 112. Maxillary plate 108 includes a plurality of holes 111 for affixing plaster 113 and maxillary study cast 115. Bracket 110 includes an adjustment screw 114 threadingly engaging therewith at bore 116 for adjusting the vertical position of incisal pin 18. Pin 18 includes a vertical guide channel 118 for receiving screw 114.

Referring now to FIGS. 6A, 6B, and 6C, mandibular support 16 of madibular facebow 12 includes a lower support arch 120 mounted on end brackets 122, 124. The ends 88, 90 of lower support arch 120 are fastened to brackets 122, 124 by screws 126. Mandibular support 16 further includes a mandibular plate 130 affixed to the mid-portion of lower support arch 120 by bracket 132. Mandibular plate 130 includes a plurality of holes such as at 136 to hold the plaster 140 on the mandibular study cast 142. The extreme end 138 of mandibular plate 130 is dimensioned to engage and support the lower end of incisal pin 18. Through the use of adjustment screw 114, the distance between maxillary plate 108 and mandibular plate 130 may be adjusted.

In operation, study casts 115, 142 of the patient's mouth are made by taking impressions using an elastic impression material such as alginate, hydrocolloid, silicon, or rubber base, and the study casts 115, 142 are each made by pouring into the elastic impression a hard artificial stone. Preoperative casts 115, 142 are used for the study of occlusal relations for diagnosis, treatment planning, and method and type of therapy. Labial cores 44, 66 are constructed for recording the movement of the mandibular.

Figure 7:
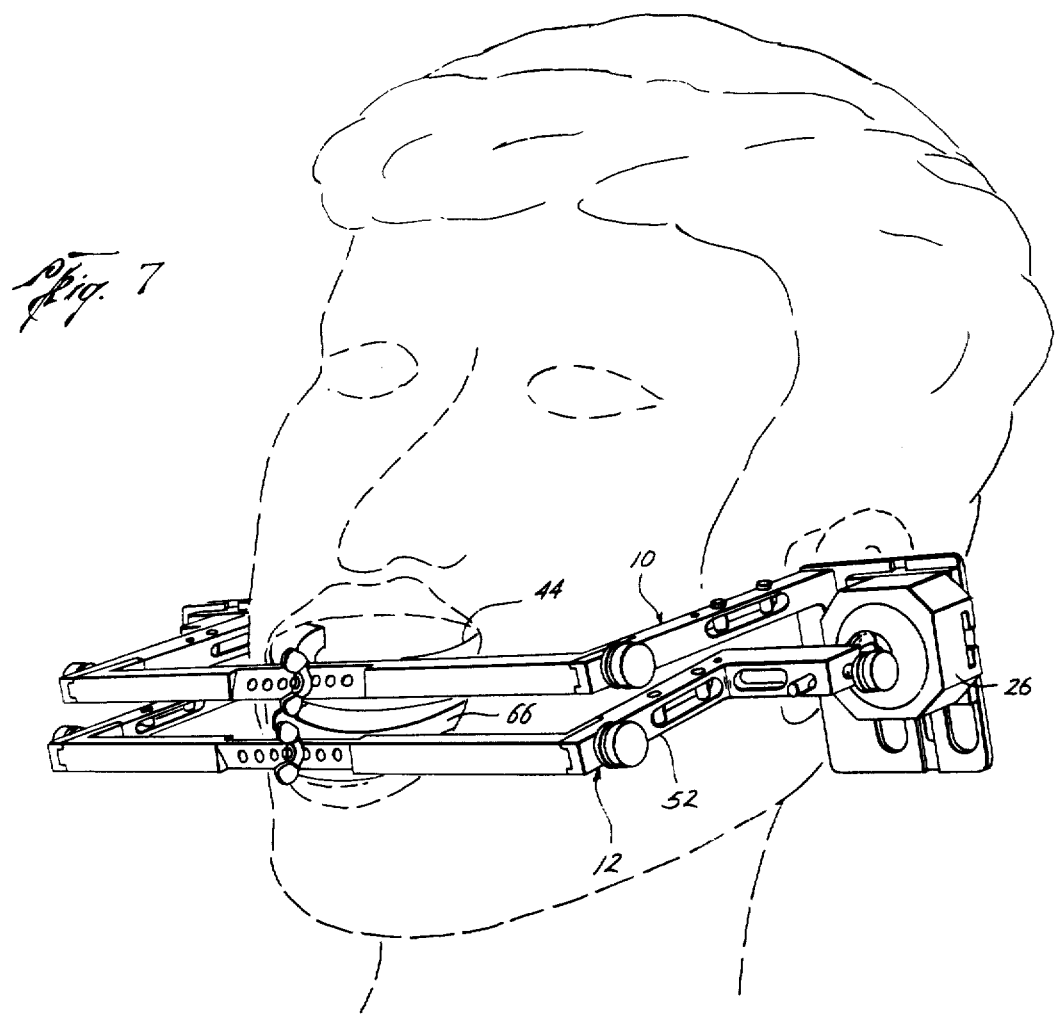
FIG. 7 is a prospective view of the maxillary and mandibular facebows in place on a patient.

As shown in FIG. 7, the maxillary and mandibular facebows 10, 12 are mounted on the patient to record the movement of the mandibular. Labial cores 44, 66 are mounted on the maxillary and mandibular facial surface for attachment to maxillary and mandibular facebows 10, 12.

In positioning the facebows 10, 12 on a patient, the styli 72 and receptacles 26, 28 are placed above the occlusal plane (the plane along which the teeth meet during closure) and anterior to the temporomandibular joint. Such positioning insures that the axis of rotation of styli 72 in receptacles 26, 28 will cause the tip of styli 72 to move anteriorly from centric relation as the patient opens his mouth. Although the present invention would operate even though the facebows 10, 12 were located other than in the preferred position, the styli 72 could move back and/or down within receptacles 26, 28 preventing the centric relation record from being the deepest impression within the plastic of the receptacles 26, 28. However, as has been indicated, the innerocclusal record need not be centric relation or centric occlusion since the present invention will function using an innerocclusal record taken at any position. Means may be provided on the facebow 10 for supporting the facebow 10 on the patient. Such means could include ear plugs mounted on facebow 10 which fit within the ear.

Receptacles 26, 28 are filled with a self-polymerizing plastic and styli 72 mounted on side arms 52, 54 of mandibular facebow 12 are inserted into the plastic of the receptacles. An innerocclusal record is taken at any position to establish a base position of the maxillary and mandibular teeth for later properly relating the upper cast 115 to the lower cast 142. The patient then makes various movements with the jaw and the styli 72 form multiple imprints in the plastic within the receptacles 26, 28.

Figure 8:
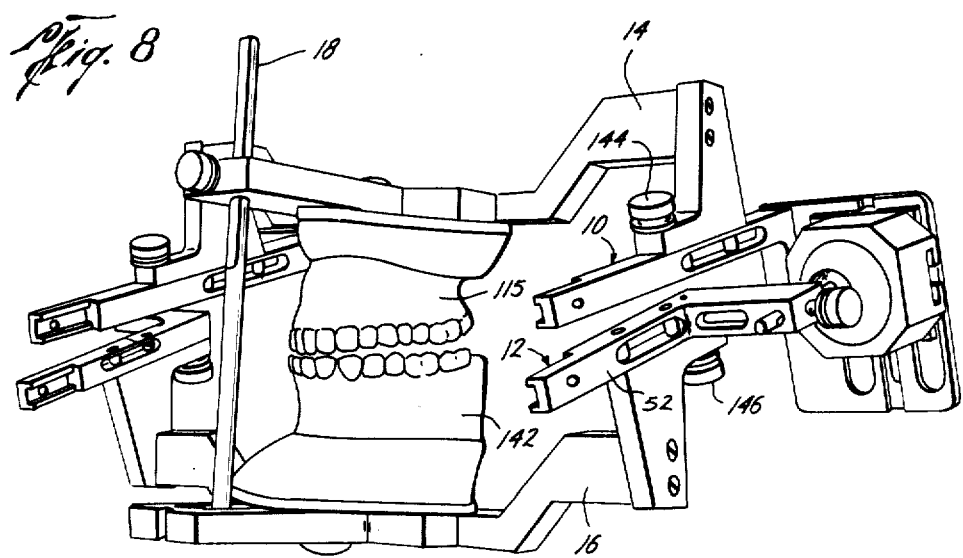
FIG. 8 is a prospective view of the stone casts mounted on the maxillary and mandibular support arches in position with the maxillary and mandibular facebows having been removed.

Referring now to FIG. 8, the upper and lower stone casts 115, 142 of the patient's teeth are then mounted on labial cores 44, 46 respectively. Maxillary and mandibular supports 14, 16 are mounted on facebows 10, 12 respectively, aligned thereto by guide pins 42, 76, and affixed thereto by mounting screws 144, 146. The upper and lower stone casts 115, 142 are properly oriented and related to each other using the innerocclusal record and are then plastered into place onto maxillary plate 108 and mandibular plate 130 with the holes 111, 136 in those plates holding the plaster 113, 140 thereto.

The vertical incisal pin 18 is mounted and set within bore 116 of bracket 110 and in engagement with mandibular plate end 138. Cross-bars 20, 50 of maxillary and mandibular facebows 10, 12 are then removed. Vertical pin 18 stabilizes the movement of the simulator. A vertical pin can be positioned on the occlusal table for customizing a plastic incisal guidance.

The imprint of the styli 72 in the plastic permits the duplication of jaw movement by stone casts 115, 142 including the terminal horizontal axis of condylar rotation, the vertical axis of condylar rotation, the sagittal axis of condylar rotation, the simultaneous multiple axes of rotation during condylar translations, the straight protrusive pathways of each condyle, the pathways of each condyle during straight lateral excursions of the mandible, and the multiple pathways of each condyle during all possible excursions of the mandible between straight lateral and straight protrusion.

Further, the action of the mandible is captured in its movement in the three horizontal, vertical, and sagittal planes and the movements caused by rotation about three different centers-horizontal (transverse axis), vertical, and sagittal. Although during function the movement of these planes and rotation about these centers occur simultaneously, the present invention does not require their precise location or registration since they are automatically reproduced during the movement of the mandibular facebow 12 within the imprints. No registrations need be transferred and the present invention does not require a centric relation record or centric occlusion record or registration since they are automatically reproduced during the movement of mandibulary facebow 12 within the imprints of the plastic. No registrations need be transferred to a mechanical counterpart, such as an articulator, whose mandibular member is so constructed that it is also supposed to move in those same three planes with rotation about those same three centers.

The present simulator is sturdy and exact in construction, is simple but efficient in mechanics of operation, and is capable of maintaining constant in duplicating desired movements.

Thus, the purpose of the simulator is achieved by reproducing effectively the mandibular movements of a patient at the laboratory bench. Because of its accuracy in the simulation of the jaw movement, the result is a better fabricated prosthesis. Further, such accuracy of simulation allows for more accurate occlusal relationships in the restorations and only requires minor adjustments after installation. It is believed that the present invention achieves maximum balancing between obtaining proper restoration within reasonable limits of time consumption and reasonable expertise and quality of results.

One of the important basic objectives is that patients must have the capability of reaching their maximum closure comfortably from many positions of the mandible without tooth interference. It is believed that in the use of the present invention reflective or interceptive occlusal contact can be prevented in the centric positions to avoid uncontrolled triggering of parafunctional or peridontal insult. The ultimate objective, of course, is to prevent faulty functional movements that result in restorations which cause peridontal breakdown of the remaining teeth, temporomandibular joint disorders, or muscle spasm.

While a preferred embodiment of the invention has been shown and described, modifications thereof can be made by one skilled in the art without departing from the spirit of the invention.

What is claimed is:

1. A dental apparatus for mounting on the facial surfaces of the maxilla and mandible of a patient to record the movements of the patient's mandible comprising:
    a first frame having two substantially horizontal receptacles having means for mounting adjacent to the patient's head above the occlusal plane formed by the meeting of the maxilla and mandible during closure and anterior to the temporomandibula joint, said first frame having an anterior portion having means for mounting on the facial surfaces of the maxilla and mandible, said receptacles having an opening toward said anterior portion;
    a molding material disposed in said receptacles;
    a second frame having two substantially horizontal styli disposed thereon having a portion thereof projecting into said receptacles in a direction extending posteriorly of said anterior portion, said styli indenting the molding material during movement of said second frame with the mandible in the horizontal, vertical and sagittal planes for recording three dimensional jaw movement, said portions of said styli received within said receptacles moving anteriorly within said receptacles as the patient opens the mouth and posteriorly as the patient closes the mouth.

2. The dental apparatus of claim 1 wherein said first and second frames are U-shaped members having side portions adapted for positioning adjacent the sides of the patient's head and a front portion for mounting on the facial surfaces of the maxilla and mandible; said receptacles having a bore for housing said molding material; the axis of said bores and said styli being parallel to said side portions.

3. A dental apparatus for mounting on the facial surfaces of the maxilla and mandible of the patent to record and then to reproduce the three dimensional movements of the mandible, comprising:
    a first frame having two receptacles mounted thereon, said first frame having means for positioning said receptacles adjacent to the sides of the patient's head and an anterior portion having means for mounting on the facial surfaces of the maxilla and mandible of the patient, said receptacles opening toward said antieror portion;
    a molding material disposed in said receptacles;
    a second frame having two styli disposed therein, said styli projecting into said receptacles in a direction extending posteriorly of said anterior portion and forming indentations in said molding material during the three dimensional movement of the patient's mandible to make an innerocclusal record; and
    means for reproducing three dimensional movements of the patient's mandible, including
        means removably mounted on said first and second frames for attaching casts of the patient's maxilla and mandible to said first and second frames, and
        means for restricting the position of the mandible cast relative to the maxilla cast, said restricting means including said styli and said receptacles, with said styli projecting into said indentations in said molding material within said receptacles and into contact with said molding material, said molding material having hardened since being indented by movement of the patient's mandible, the mandible cast being free to move except as prevented by said restricting means.

4. A dental apparatus for recording and then reproducing the three dimensional movements of the mandible, comprising:
    an upper stationary frame having an anterior portion adapted for mounting on the patient's jaw and only two receptacles mounted thereon, said receptacles being adapted for positioning adjacent each side of the patient's head and having an opening facing towards said anterior portion, said receptacles being adapted to hold a molding material;
    a lower movable frame having an anterior portion and two styli disposed thereon, said styli projecting posteriorly into said receptacles for indenting the molding material during the three dimensional movement of the patient's mandible, said styli being the only contact with said upper stationary frame during the recording of the three dimensional movements;
    means removably mounted on said anterior portions of said upper and lower frames for attachment to the facial surfaces of the patient's maxilla and mandible, respectively, said lower movable frame being moved with respect to said upper stationary frame by the patient's mandible in all three dimensional movements in the horizontal, vertical, and sagittal planes including all arcs of closure;
    means removably mounted in said upper and lower frames for attaching casts of the patient's maxilla and mandible to said upper and lower frames; and
    said styli indentations and styli reproducing all of the three dimensional movements of the patient's mandible with the casts attached to said upper and lower frames.

5. A method of recording and duplicating the jaw movements of a patient comprising:
    mounting labial cores on a maxillary facebow and on a mandibular facebow;
    inserting the patient's head into the maxillary facebow and mandibular facebow;
    affixing the labial cores to the maxilla and mandible of the patient;
    positioning a substantially horizontal stylus, mounted on each side of the mandibular facebow, into adjacent substantially horizontal receptacles mounted on each side of the maxillary facebow;
    adjusting the horizontal styli within the receptacles;
    placing self-polymerizing acrylic in the receptacles;
    moving the patient's mandible three dimensionally in the horizontal, vertical, and sagittal planes for all positions of the mandible;

indenting the acrylic by the styli as the patient moves the jaw three dimensionally;
taking an innerocclusal record in any position;
removing the facebows from the patient's head;
preparing dental casts;
mounting maxillary and mandibular arches to the maxillary and mandibular facebows;

plastering the dental casts to the maxillary and mandibular arches; and
moving the dental casts within the limits required by the styli within the indentations of the acrylic to duplicate the three dimensional movement of the patient's jaw.

* * * * *